United States Patent
Bariska, Jr. et al.

(10) Patent No.: US 9,466,226 B1
(45) Date of Patent: *Oct. 11, 2016

(54) GENERAL PURPOSE DEVICE TO ASSIST THE HARD OF HEARING

(71) Applicant: International Business Machines Corporation, Armonk, NY (US)

(72) Inventors: Arthur J. Bariska, Jr., Tucson, AZ (US); Joel L. Masser, San Jose, CA (US); Kevin D. McKenzie, Poughkeepsie, NY (US); Eileen P. Tedesco, Sharon, CT (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/043,776

(22) Filed: Feb. 15, 2016

Related U.S. Application Data

(63) Continuation of application No. 14/887,644, filed on Oct. 20, 2015.

(51) Int. Cl.
*G09B 21/00* (2006.01)
*H04R 25/00* (2006.01)

(52) U.S. Cl.
CPC ........... *G09B 21/009* (2013.01); *H04R 25/407* (2013.01); *H04R 2225/41* (2013.01)

(58) Field of Classification Search
CPC ............ G06Q 50/24; G09G 2380/08; H04R 2225/41; H04R 25/407; H04R 25/70; H04R 27/00; H04R 3/005; H04R 1/406; H04R 2410/07; H04R 25/00; H04R 25/405; H04R 25/453; H04R 25/50; H04R 25/554; H04R 25/05; H04R 3/04; G08B 19/00; G08B 1/08; G08B 25/008; G08B 25/009; G08B 6/00; G08B 7/06; G10L 15/22; G10L 25/75; H04B 3/21; H04M 1/2155; H04M 1/2475; H04M 1/6016; H04M 1/7253; H04M 1/72591
USPC ........................................................ 340/4.14
See application file for complete search history.

(56) References Cited

U.S. PATENT DOCUMENTS

| | | |
|---|---|---|
| 5,045,833 A | 9/1991 | Smith |
| 7,109,879 B2 | 9/2006 | Stults et al. |

(Continued)

FOREIGN PATENT DOCUMENTS

WO 2008008908 A2 1/2008

OTHER PUBLICATIONS

Heckendorf, Stacie, "Chapter 13—Assistive Technology for Students who are Deaf or Hard of Hearing", WATI, Assessing Students' Needs for Assistive Technology (2009), pp. 1-19.

(Continued)

*Primary Examiner* — Fekadeselassie Girma
(74) *Attorney, Agent, or Firm* — Gilbert Harmon, Jr.

(57) ABSTRACT

An approach to notifying a person who is hard of hearing of audible events based on a configurable device. The device has microphones and associated buttons mounted on its surface. The user programs the device by depressing a selected button longer than a preconfigured time to place the device in listen mode. The user generates the desired audible event and the device records the audible event. The selected button is depressed again to instruct the device to associate the audible event with a visual alarm indicator of colored/flashing lights and/or a text projection. The device listens for the audible event and activates the visual alarm indicator when the device detects the audible event.

1 Claim, 4 Drawing Sheets

(56) References Cited

U.S. PATENT DOCUMENTS

| | | | |
|---|---|---|---|
| 7,675,407 B2 | 3/2010 | Yuk et al. | |
| 7,847,970 B1* | 12/2010 | McGrady | G06F 19/3456 345/179 |
| 8,682,042 B1* | 3/2014 | Manion | G06Q 10/00 382/128 |
| 2007/0018798 A1* | 1/2007 | Chen | B60R 25/1003 340/425.5 |
| 2007/0033055 A1* | 2/2007 | Tanaka | G10L 15/22 704/275 |
| 2012/0128187 A1* | 5/2012 | Yamada | H04R 25/407 381/313 |
| 2013/0226593 A1* | 8/2013 | Magnusson | H04N 5/765 704/276 |
| 2013/0243227 A1 | 9/2013 | Kinsbergen et al. | |
| 2014/0211971 A1 | 7/2014 | Sohn et al. | |
| 2014/0219474 A1* | 8/2014 | Feldt | H04R 3/005 381/98 |
| 2015/0010179 A1 | 1/2015 | Solum | |
| 2015/0011266 A1* | 1/2015 | Feldt | H04M 9/082 455/570 |
| 2015/0078600 A1* | 3/2015 | Rasmussen | H04R 25/405 381/318 |
| 2015/0078602 A1* | 3/2015 | Sohn | H04R 25/604 381/328 |
| 2015/0163602 A1* | 6/2015 | Pedersen | H04R 25/554 381/315 |
| 2015/0199919 A1 | 7/2015 | Ander et al. | |
| 2015/0222996 A1* | 8/2015 | Chu | H04R 25/40 381/313 |
| 2016/0073203 A1* | 3/2016 | Kuriger | H04R 25/43 381/23.1 |

OTHER PUBLICATIONS

Bariska et al., "General Purpose Device to Assist the Hard of Hearing", U.S. Appl. No. 14/887,644, filed Oct. 20, 2015, 23 pages.
IBM Appendix P, patents or patent applications treated as related, Apr. 15, 2016, 2 pages.

\* cited by examiner

GENERAL PURPOSE DEVICE TO ASSIST THE HARD OF HEARING

BACKGROUND OF THE INVENTION

The present invention relates generally to the field of hearing impairment assistance, and more particularly to devices for notifying the hearing impaired of configured events.

Hearing loss can result from a variety of issues such as, but not limited to, aging, long-term exposure to loud noise, short-term exposure to very loud noise and genetic limitations. Examples of existing solutions to these issues comprise hearing aids and various types of implants but these solutions require the user to have the discipline to wear the hearing aid or submit to the cost and invasiveness of a surgical procedure. Further, the user requires access to infrastructure associated with these solutions such as, but not limited to, batteries, audiologists, surgical facilities, etc. Many users either do not have access to these solutions or cannot afford the cost.

Special purpose devices are available for connecting to specific household objects emitting sound notifications such as telephones, doorbells, alarm clocks, etc. for providing either sound amplification or alternative alert mechanisms (e.g., illumination indicators or vibrational indicators). Similar issues arise as previously described related to availability, cost and compatibility with existing infrastructure. For example, compatibility issues related to wiring codes, phone jack design and configuration and other connection related requirements. Further, based on the single-purpose nature of these devices, multiple devices may be required to meet a user's needs, leading to higher costs and operational considerations.

SUMMARY

According to an embodiment, an apparatus for notifying hard of hearing individuals of audible events, the apparatus comprising: a power supply for powering the apparatus; one or more microphones, wherein the one or more microphones are tuned to different frequencies, for detecting sound associated with one or more audible events and generating an associated independent visual alarm for the one or more audible events and wherein any sound louder than a preconfigured level is associated with a preconfigured audible event; one or more momentary contact buttons wherein at least one of the one or more buttons are associated with at least one of the one or more microphones for configuring the associated microphone to detect a selected audible event and for acknowledging any of the associated independent visual alarms; one or more visual indicators wherein at least one of the one or more visual indicators is configured to activate, based on the associated independent visual alarm, when the selected audible event is detected and wherein the one or more visual indicators are at least one of different colored lights, flashing lights, strobe lights, a text projector and a display; a control computer for controlling operations comprising one or more inputs associated with the one or more buttons, one or more inputs associated with the one or more microphones, one or more outputs associated with the one or more visual indicators, determining a function of the one or more buttons based on how long the one or more buttons are depressed and determining the direction of the sound based on the different frequencies of the one or more microphones; and a shell for mounting the power supply, the one or more microphones, the one or more buttons, the one or more visual indicators and the control computer wherein the shell has a plurality of facets and the one or more microphones are attached to a portion of the plurality of facets and one of the plurality of facets is a base suitable for placement on a flat surface.

DETAILED DESCRIPTION

Embodiments of the present invention disclosed herein recognize a need for a general purpose device to assist the hard of hearing. For example, audible alerting devices such as a telephone, a doorbell, a smoke/carbon monoxide detector, a fire alarm and an oven timer have different interfaces for a communicative connection or no communicative connection capabilities for providing an alternative notification method for those people who are hard of hearing. Embodiments of the present invention can avoid this problem by detecting the audible alert and transform the audible alert into a different visual alert associated with each of the audible alerts.

Embodiments of the present invention will now be described in detail with reference to the accompanying figures. It is to be understood that the disclosed embodiments are merely illustrative of potential embodiments of the present invention and may take various forms. In addition, each of the examples given in connection with the various embodiments is intended to be illustrative, and not restrictive. Further, the figures are not necessarily to scale, and elements and features can have different dimensions than those depicted in the figures. Therefore, specific structural and functional details disclosed herein are not to be interpreted as limiting, but merely as a representative basis for teaching one skilled in the art to variously employ the present invention.

References in the specification to "an exemplary embodiment," and "other embodiments," etc., indicate that the embodiment described may include a particular feature, structure or characteristic, but every embodiment may not necessarily include the particular feature, structure or characteristic. Further, when a particular feature, structure, or characteristic is described in connection with an embodiment, it is submitted that it is within the knowledge of one skilled in the art to affect such feature, structure or characteristic in connection with other embodiments whether or not specifically described.

Figure 1:
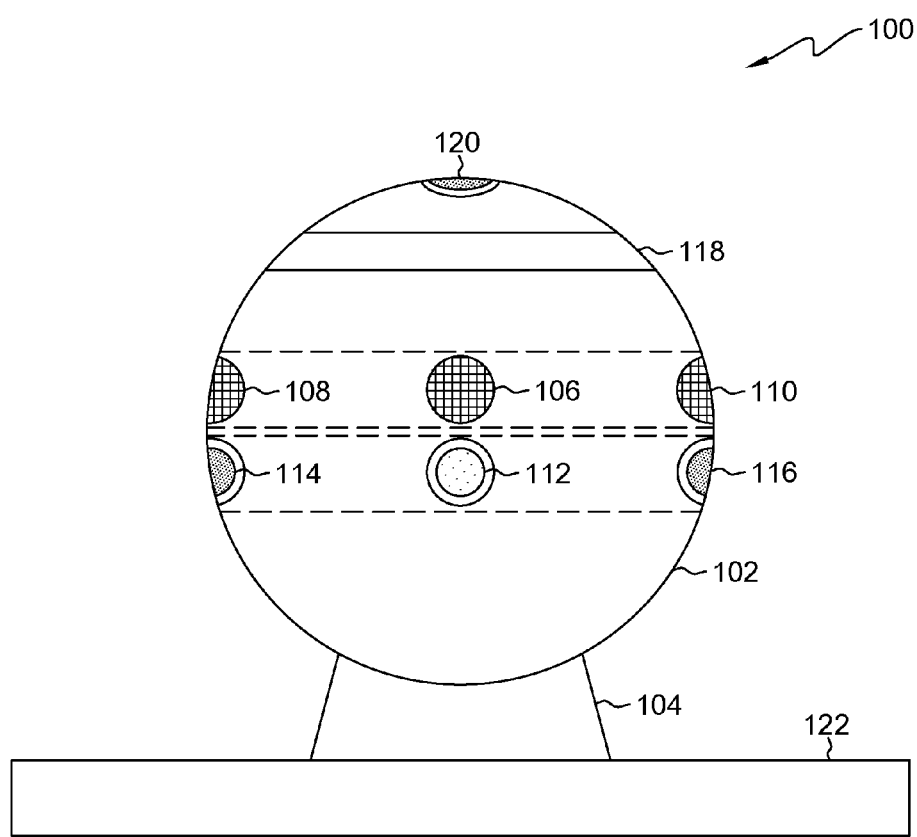
FIG. 1 is an exterior perspective view of a spherical apparatus for assisting the hard of hearing, in accordance with an embodiment of the present invention.

FIG. 1 is a perspective diagram of a spherical apparatus 100 for assisting the hard of hearing, in accordance with an embodiment of the present invention. A sphere 102 attached to a stand 104 allowing the sphere 102 to sit on a flat surface 122 found in a home. Examples of the stand 104 comprise a one-piece base or a plurality of legs suitable for allowing placement of the apparatus on a surface. The sphere 102 has a plurality of microphones 106, 108, 110 (others not visible)

mounted on its surface wherein the plurality of microphones 106, 108, 110 are distributed around the surface of the sphere 102. In one embodiment, the microphones 106, 108, 110 are equally spaced around a cross section of sphere 102 in a radial pattern. In another embodiment, each microphone 106, 108, 110 is tuned to a different frequency, i.e. pitch, allowing better detection of expected sounds and determination of the direction of the sound source.

Continuing with the embodiment, a visual indicator 118 can be integrated into the sphere 102 allowing observation from any direction around the sphere 102. For example, the visual indicator 118 can be a multi-colored light providing a different color for each expected sound or it can be a single color or strobe light flashing a preconfigured number of flashes for each expected sound. In another example, the visual indicator 118 can be a text projector, projecting a preconfigured text message associated with receipt of an expected sound. In another aspect of the embodiment, a display screen can be mounted on the surface of the apparatus providing for messages viewable on the display screen.

In another aspect of an embodiment, the sphere has a plurality of buttons 112, 114, 116 (others not visible) for configuring the device for detecting individual sounds. In one embodiment, each button is associated with a sound on which to alert and can be a momentary contact button. A user depresses and holds one of the buttons 112, 114, 116 for a sufficient period of time such as, but not limited to, until the visual indicator 118 activates to provide notice to begin recording an expected sound, the user then releases the button and generates the expected sound. For example, the user rings the doorbell. Next, the user depresses the same button to end recording when the expected sound is complete. In this aspect of the embodiments, repeating the configuration with different buttons for different sounds, the device can be configured, i.e., instructed, to listen for different sounds and display a distinctive visual indication when each recorded sound is detected. In another aspect of the embodiments, a default visual indication can be displayed for sounds exceeding a preconfigured loudness threshold that do not match any of the recorded sounds. An alarm acknowledgment button 120 of the embodiments provides for canceling the visual indicator 118 once the hearing impaired individual has observed the visual indicator 118. In another aspect of the embodiments, the visual indicator 118 can be configured to deactivate when the expected sound stops or after a preconfigured amount of time after the expected sound stops.

The sphere 102 has a control computer (not shown) for managing the inputs, e.g., the microphones 106, 108, 110 and the buttons 112, 114, 116, and the outputs, e.g., the visual indicator 118. The control computer provides the capability to determine the amount of time a button 112, 114, 116 is depressed allowing the buttons 112, 114, 116 to function in a plurality of capacities. For example, if a button 112, 114, 116 is depressed greater than a predetermined time period then the button 112, 114, 116 functions to place the control computer in audible event recording mode, allowing the user to generate a sound to be associated with an audible event. If the button 112, 114, 116 is depressed less than a predetermined time period then depressing the button 112, 114, 116 functions to acknowledge the user has observed the visual indicator associated with the audible event.

Figure 2A:
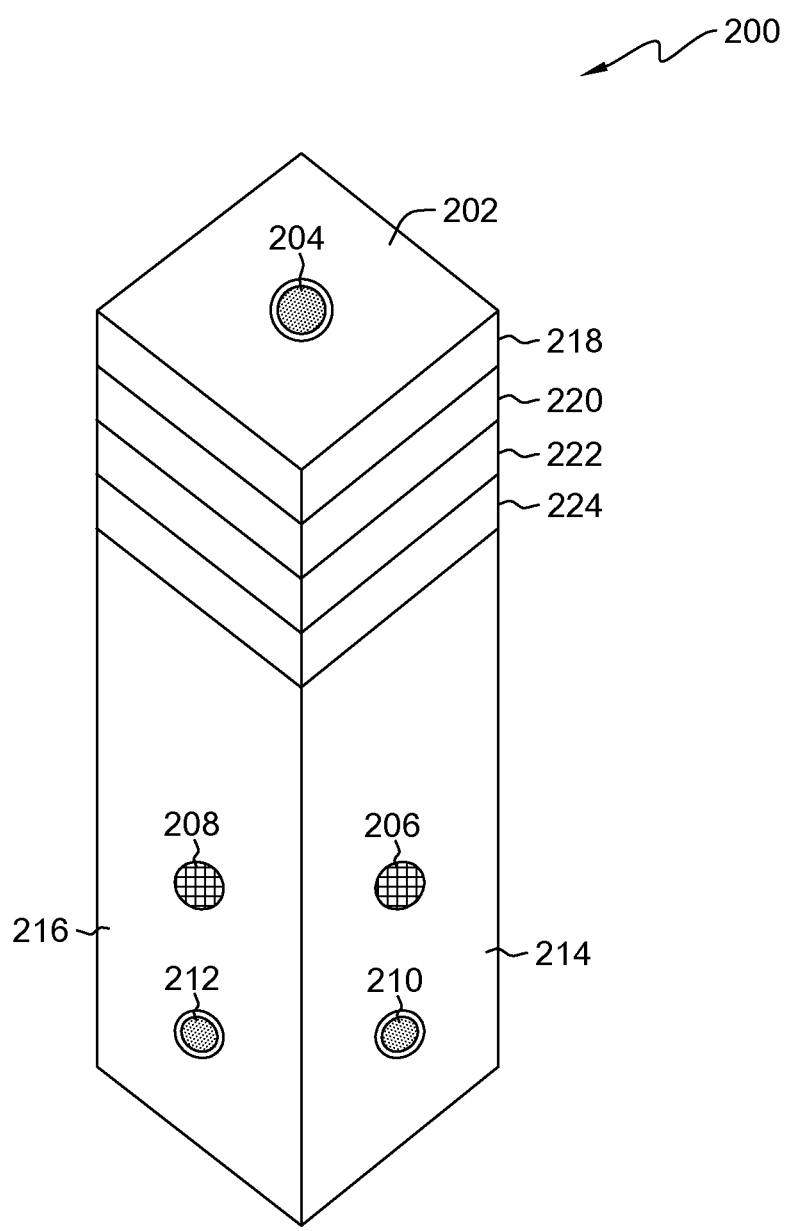
FIG. 2A-B is an exterior perspective view of a cuboid apparatus and a pyramidal frustum apparatus, respectively, for assisting the hard of hearing, in accordance with an embodiment of the present invention.

Continuing, FIG. 2A depicts cuboid apparatus 200 for assisting the hard of hearing, in accordance with an embodiment of the present invention. The cuboid uses one face as a base (i.e., bottom face) and four faces, perpendicular to the base, of which two faces 214, 216 are visible for mounting a microphone 206, 208 a button 210, 212 and a plurality of visual indicators 218, 220, 222, 224 on each face. It should be noted that although not visible, the other two faces are similarly configured. The microphones 206, 208 and buttons 210, 212 perform similarly as described for the microphones 106, 108, 110 and buttons 112, 114, 116 associated with FIG. 1. It should be noted that a face can be described as a facet.

The cuboid apparatus 200 in this embodiment has 4 visual indicators 218, 220, 222, 224 for alerting the user to the occurrence of a configured sound or a sound not matching any configured sound but louder than a predefined loudness threshold. In one example, the visual indicators are different colored lights with one light associated with a microphone 206/button 210 pair of one of the faces 214 for a configured sound. Similarly, each microphone/button pair is associated with a different colored light or with combinations of different colored lights providing for a larger number of configured sounds than the number of individual visual indicators 218, 220, 222, 224. It should be noted that the cuboid apparatus could have a single visual indicator capable of displaying a plurality of different colors wherein a single color is associated with a microphone 206, 208/button 210, 212 pair.

Continuing with an example, when the cuboid apparatus 200 detects a configured sound, one or more visual indicators, i.e., colored lights, associated with the button used to record the sound, illuminates. It should be noted that the one or more colored lights can be configured to flash if desired. Once the user has been alerted to the sound, based on noticing the one or more flashing lights, the user can acknowledge the visual alarm by depressing an acknowledgment button 204. The top face 202 comprises an example button 204 for the user to depress to acknowledge an alarm and terminate the visual indicators 218, 220, 222, 224 as described for FIG. 1. It should be noted in the embodiment that the acknowledgment button can be located on a different face of cuboid apparatus 200 or shared with one or more buttons of the microphone 206, 208/button 210, 212 pairs.

Figure 2B:
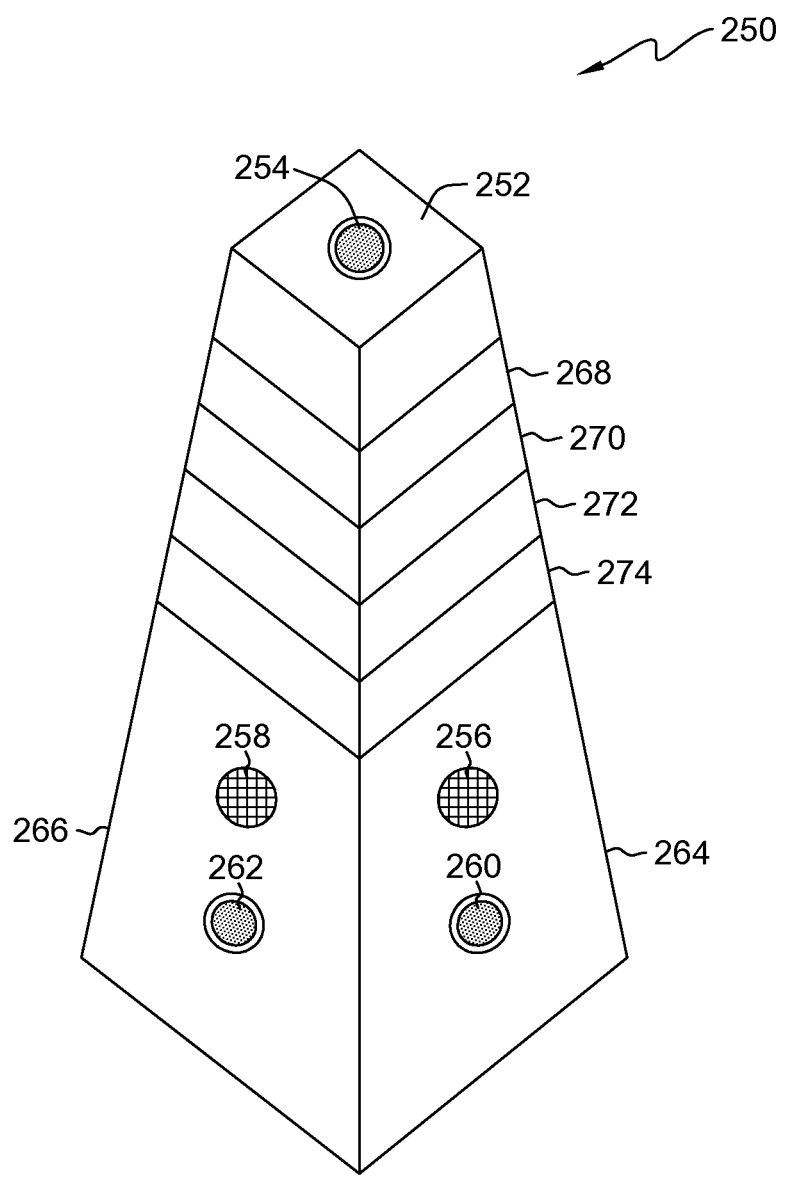

FIG. 2B depicts a pyramidal frustum apparatus 250 for assisting the hard of hearing, in accordance with an embodiment of the present invention. The pyramidal frustum uses one face as a base (i.e., bottom face) and four faces, connected to the base, of which two faces 264, 266 are visible, for mounting a microphone 256, 258 a button 260, 262 and a plurality of visual indicators 268, 270, 272, 274 on each face. It should be noted that although not visible, the other two faces are similarly configured. The microphones 256, 258 and buttons 260, 262 perform similarly as described for the microphones 206, 208 and buttons 212, 214 associated with FIG. 2A. The top face 252 comprises a button 254 for the user to depress to acknowledge an alarm and terminate the visual indicators 268, 270, 272, 274 as described for FIG. 2A. Further, the capabilities and behavior of the pyramidal frustum apparatus 205 of FIG. 2B are similar to that as described for the cuboid apparatus 200 of FIG. 2A.

Further, the user can transport each of the previously described apparatuses 100, 200, 250 to other locations for use. The apparatuses 100, 200, 250 do not require reconfiguration for use at another location, e.g., hotel, office, etc., but can be configured for additional sounds if necessary. As previously described, unknown noises, i.e., not previously configured, can be set to alarm if the noise is louder than a preconfigured level to protect the user against unknown alarm conditions or known alarm conditions that are not configurable because it is not possible to generate the alarm, e.g., fire alarm, tornado warning, air raid, etc., for configuration. It should be noted that other emergency, e.g., noxious gas, or natural disaster audible notices can be configured for detection.

Figure 3:
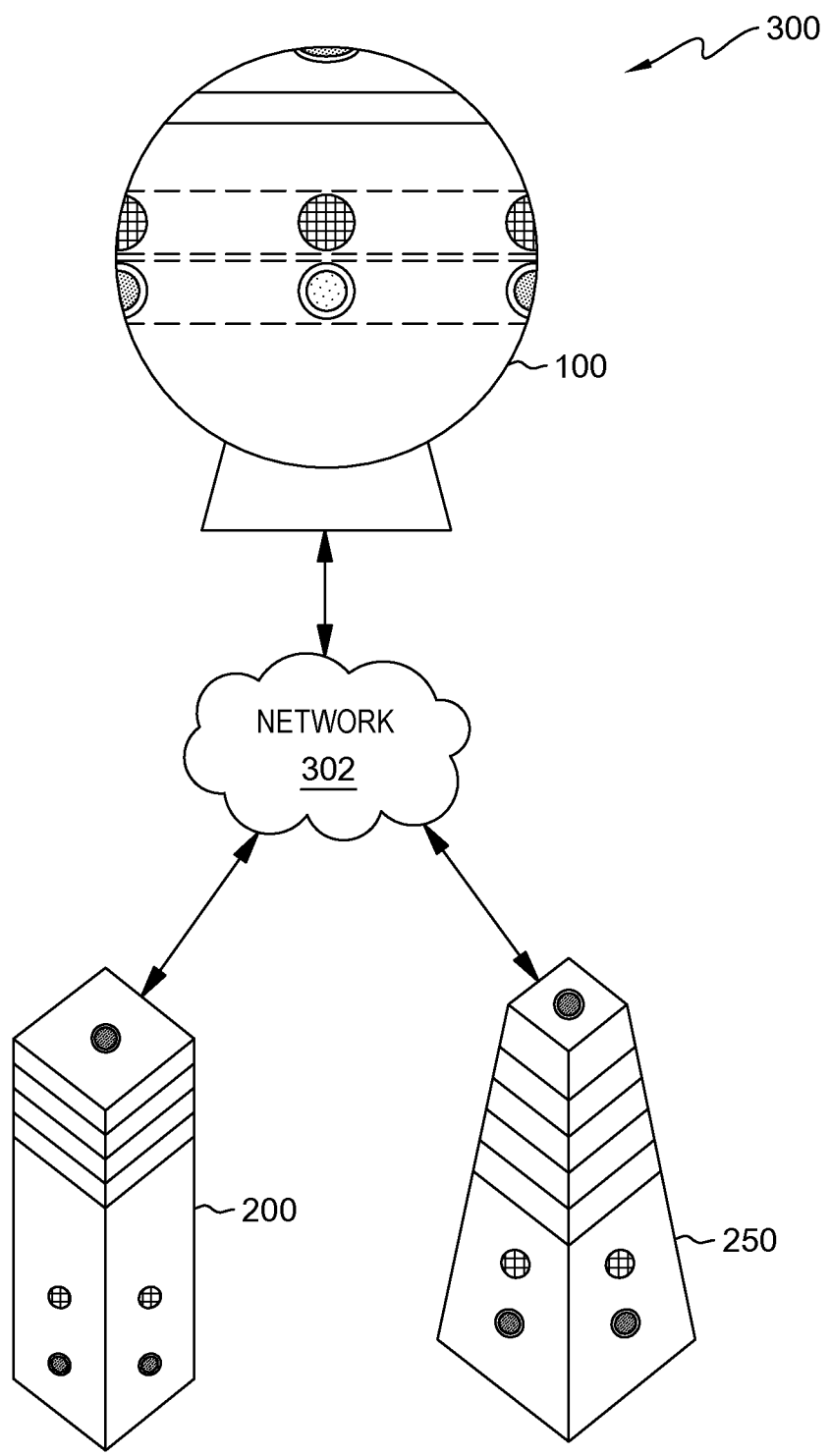
FIG. 3 is an exterior perspective view of a plurality of apparatuses connected by a communications network for assisting the hard of hearing, in accordance with an embodiment of the present invention.

Turning now to FIG. 3, a system 300 of for assisting the hard of hearing, in accordance with an embodiment of the present invention. The system 300 comprises the previously described spherical apparatus 100, cuboid apparatus 200 and the pyramidal apparatus 250 interconnected via a network 302 component. Each of the previously described apparatuses 100, 200, 250 additionally can have wired and/or wireless network communication capabilities such as, but not limited to, WiFi, Bluetooth and Mesh based protocols for communicating with each other. For example, when one of the apparatuses 100, 200, 250 detects a sound, the detecting apparatus, e.g., the spherical apparatus 100, can communicate the detection to the other networked apparatuses, e.g., the cuboid apparatus 200 and the pyramidal apparatus 250, allowing the network of apparatuses 100, 200, 250 to cooperate and distinguish noises from each other. Accordingly, the networked apparatuses 100, 200, 250 can work together to determine the originating direction of the detected noise. Further, each networked apparatus 100, 200, 250 can be configured to display an alarm indication and/or allow acknowledgment of an alarm.

In another aspect of the embodiment depicted by the system 300, the networked apparatuses 100, 200, 250 can integrate through the network communications with other household devices capable of communicating through communication protocols supported by the system 300 and the household devices. For example, other household devices could detect external alarms or internally generated alarms and report, via the network 302 component, these alarms to one or more of the apparatuses 100, 200, 250. In this manner, the system 300 can alert the user to an alarm condition associated with an aspect of the surrounding environment without the need to program the apparatuses 100, 200, 250 to detect the alarm. For example, home security systems could provide notice of security breaches such as, but not limited to, open doors or windows, appliances could provide notice of out of specification conditions, such as, but not limited to, a refrigerator or freezer temperature too high because of an open appliance door and smart televisions could provide local early warning notifications for imminent weather conditions.

Further, the communication capabilities of the system 300 can include the capability to communicate over a network 302 component connection supporting protocols allowing internet communication and/or communication over a telephone system. It should be noted that the communication capabilities of the apparatuses and the network 302 component are managed by the control computers (not shown) associated with each apparatus. For example, the apparatuses 100, 200, 250 can send alarm notifications to persons outside of the local environment by methods such as, but not limited to, email, text messages, audio streams or recorded audio clips. In another aspect, video cameras could be incorporated in the apparatuses 100, 200, 250 and video streams or recorded video clips could be sent as notifications to persons outside of the local environment. It should be noted that the previously described notification methods can be configured to alert individually or simultaneously and can be acknowledged locally and/or remotely. It should be noted that the notifications can be configured for different destinations. For example, a detected smoke alarm can result in a notification to the fire department, a detected security alarm, e.g., open window or door, can be directed to the police department and a detected appliance alarm, e.g., the stove on longer than a preconfigured time or a refrigerator/freezer temperature too high can be directed to a family member or a neighbor for resolution.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. An apparatus for notifying hard of hearing individuals of audible events, the apparatus comprising:
    a power supply for powering the apparatus;
    one or more microphones, wherein the one or more microphones are tuned to different frequencies, for detecting sound associated with one or more audible events and generating an associated independent visual alarm for the one or more audible events and wherein any sound louder than a preconfigured level is associated with a preconfigured audible event;
    one or more momentary contact buttons wherein at least one of the one or more buttons are associated with at least one of the one or more microphones for configuring the associated microphone to detect a selected audible event and for acknowledging any of the associated independent visual alarms;
    one or more visual indicators wherein at least one of the one or more visual indicators is configured to activate, based on the associated independent visual alarm, when the selected audible event is detected and wherein the one or more visual indicators are at least one of different colored lights, flashing lights, strobe lights, a text projector and a display;
    a control computer for controlling operations comprising one or more inputs associated with the one or more buttons, one or more inputs associated with the one or more microphones, one or more outputs associated with the one or more visual indicators, determining a function of the one or more buttons based on how long the one or more buttons are depressed and determining the direction of the sound based on the different frequencies of the one or more microphones; and
    a shell for mounting the power supply, the one or more microphones, the one or more buttons, the one or more visual indicators and the control computer wherein the shell has a plurality of facets and the one or more microphones are attached to a portion of the plurality of facets and one of the plurality of facets is a base suitable for placement on a flat surface.

* * * * *